United States Patent [19]

Suzuki

[11] Patent Number: 5,426,942
[45] Date of Patent: Jun. 27, 1995

[54] METHOD AND APPARATUS FOR DRIVING MICROBODIES

[75] Inventor: Makoto Suzuki, Tsukuba, Japan

[73] Assignees: Agency of Industrial Science and Technology; Ministry of International Trade and Industry, both of Tokyo, Japan

[21] Appl. No.: 135,562

[22] Filed: Oct. 14, 1993

[30] Foreign Application Priority Data

Oct. 14, 1992 [JP] Japan .................. 4-301749

[51] Int. Cl.⁶ .............................................. F03G 7/00
[52] U.S. Cl. ............................................. 60/721
[58] Field of Search ................................. 60/721

[56] References Cited

U.S. PATENT DOCUMENTS 5,226,292  7/1993  Urry ........................ 60/721

Primary Examiner—Ira S. Lazarus
Assistant Examiner—L. Heyman
Attorney, Agent, or Firm—Oblon, Spivak, McClelland, Maier, & Neustadt

[57] ABSTRACT

A method and apparatus for driving one or multiple microbodies having a size in the order of several nanometers, using a relatively simple system structure that does not require the use of large peripheral devices. Each body moves along a substrate that is hydrophobic at a low temperature and hydrophilic at a high temperature, and consists of an attachable flexible portion at the front and a detachable flexible portion adjoining the rear of the attachable flexible portion.

15 Claims, 3 Drawing Sheets

METHOD AND APPARATUS FOR DRIVING MICROBODIES

BACKGROUND OF THE INVENTION

1. Field of the Invention

This invention relates to a method and apparatus for simultaneously driving numerous microbodies having dimensions in the order of several nanometers, micrometers or millimeters that can be utilized in such fields as engineering, medicine and pharmacology as a source of motive power for artificial muscles and ultrasmall mechanisms and the like, such as micromachines, nanomachines and controlled-release pharmaceuticals, for example.

2. Description of the Prior Art

As conventional methods of driving microbodies, there are known methods such as those that utilize piezoelectric elements, or electrostatic or ultrasonic motors, or optical forceps formed by finely collimated light beams. More recently a fine probe such as that of a scanning tunneling microscope (STM) or atomic-force microscope (AFM) has been used to manipulate microscopic particles, atoms and molecules.

The above-mentioned conventional techniques that can drive the smallest bodies are the optical forceps method, the STM method and the AFM method. In the case of the optical forceps method it is necessary to aim a fine, external light beam at the particle to be driven. The light beam has to be very fine to match the microscopic dimensions of the particles being handled, so means such as a microscope is used to focus the beam to the requisite fineness. It follows, therefore, that in order to simultaneously drive numerous microbodies, it is necessary to use numerous fine light beams, and that a method of using these beams to scan the particles at high speed is needed. The result is that it becomes necessary to use a very large external apparatus to move a microscopic body the smallest of distances. Even if, instead of the numerous light beams, an optical scanning arrangement were to be used in which the beam intensity was modulated on a time basis, the result would still be the use of large peripheral devices to drive microscopic bodies. The same problem arises with respect to the STM and AFM methods, as both require the use of a fine probe, and preparing this probe requires the use of large peripheral devices.

Also, while piezoelectric elements can be used to control quite small bodies, again, quite a large external piezoelectric element is required for the slightest movement of a microscopic body.

The problem is the same with ultrasonic motors, because of the large size of the elements used. With an ultrasonic motor, an ultrasonic wave is focused on a particle of interest to move the particle. However, ultrasonic waves cannot be focussed on a point with the same precision as a light beam, and this relatively lower precision restricts the particles that can be controlled by ultrasonic waves to those having a size in the micrometer range, so a problem with this method is that it cannot be applied to smaller particles, that is, to nanometric particles.

Electrostatic motors, ultrasonic motors, piezoelectric elements and the like all require an array of electrodes or oscillators, each of which is about the same size as the body to be driven. As such, the smaller the size of the bodies which are to be driven, the more difficult it is to fabricate such electrode or oscillator arrays, and as the electrodes or oscillators have to be connected to enable them to be electrically energized, the structure is complex.

SUMMARY OF THE INVENTION

The object of the present invention is therefore to provide a method and apparatus for driving one or for simultaneously driving multiple microbodies having a size in the order of several nanometers, using a relatively simple system structure that does not require the use of large peripheral devices.

The above object is attained in accordance with the present invention by a method for driving microbodies, comprising one or multiple bodies to be driven provided on a substrate in a spaced arrangement in one line, maintaining the substrate and the bodies in a liquid, wherein said at least one body to be driven consists of an attachable flexible portion disposed in a direction of forward movement and a detachable flexible portion adjoining the rear of the attachable portion, the substrate is formed of a material that is hydrophobic at a low temperature region and hydrophilic at a high temperature region, the attachable portion and detachable portion are formed of a material that is hydrophobic at both the low and high temperature regions, the detachable portion can be heated to a temperature within or above the high temperature region while the liquid and substrate are maintained in the low temperature region, the attachable portion is formed so that even when the detachable portion is heated, there is a portion in contact with the substrate that is in the low temperature region, and by heating the detachable portion to a temperature in the high temperature region, a hydrophobic interaction causes the detachable portion to be repeatedly adsorbed and released while the attachable portion remains attached to the substrate, thereby causing the body to be moved forward in steps along the substrate.

The above object is also attained by a microscopic body drive apparatus, comprising a substrate formed of a material that is hydrophobic at a low temperature region and hydrophobic a a high temperature region, at least one body to be driven arranged on the substrate facing a prescribed direction, said body to be driven being comprised of an attachable flexible portion disposed in a direction of forward movement and a detachable flexible portion adjoining the rear of the attachable portion, said attachable portion and detachable portion both being formed of a hydrophobic material, an aqueous liquid into which the substrate and the body to be driven are both immersed which maintains the substrate at a low temperature region, and means for selectively heating the detachable portion whereby the portion of the substrate in contact with the detachable portion is heated to cause it to become hydrophilic.

Thus, in this invention, a body to be driven consisting of an attachable portion and an adjoining detachable portion at the rear is arranged on a substrate in a liquid, and the attachable and detachable portions are both formed of a hydrophobic material, and the substrate is formed of a material that is hydrophobic at a low temperature region and hydrophobic at a high temperature region, and by heating only the detachable portion the portion of contact with the substrate is heated, causing it to become hydrophilic, so that when the detachable portion is separated from the substrate by the liquid, a sliding force acts on the body, causing it to move forward with the attachable portion attached to the substrate, When the detachable portion reaches the hydrophobic portion of the substrate where the attachable portion was in contact, it heats up in contact with the substrate, causing it to become hydrophilic and again become detached. Repeating this sequence causes the body to be moved ahead along the substrate. When the attachable and detachable portions are both hydrophilic, the same operation can be achieved by using an oil as the liquid.

The above method in which the detachable portion is heated by light or electromagnetic radiation can be used to readily drive a plurality of bodies simultaneously.

Further features of the invention, its nature and various advantages will be more apparent from the accompanying drawings and following detailed description of the invention.

DESCRIPTION OF THE PREFERRED EMBODIMENT

Figure 5:
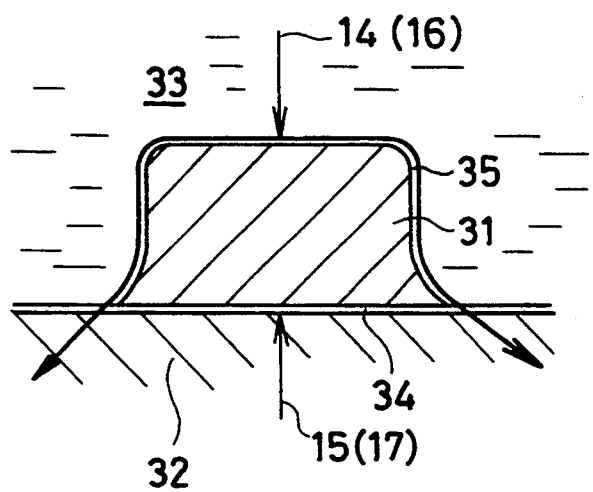
FIG. 5 illustrates the force of adsorption produced by the interaction between the hydrophobic bodies.

The microbody drive method of this invention uses adsorption provided by a hydrophobic interaction as the driving force, so the description will begin with an explanation of the adsorbing force resulting from the hydrophobic interaction. FIG. 5 shows a microscopic, pliant body 31 in water 33 on a plate 32. If both the body 31 and the plate 32 are made hydrophobic, there will be no entry of the water 33 into the interface 34 between body 31 and plate 32, so a boundary 35 (indicated in the drawing by a thick line) between the water 33 and the body 31 will only form around on the outer surface of the body 31. Thus, the force 14 produced by the surface tension of the water 33 will act to press the body 31 onto the plate 32, which gives rise to a reactive force 15 by the plate 32, so the effect of these forces is to press the body and plate together. Also, if the body 31 and plate 32 are both hydrophilic and the liquid is an oil, the effect will again be for the body 31 and plate 32 to be pressed together.

Figure 1:
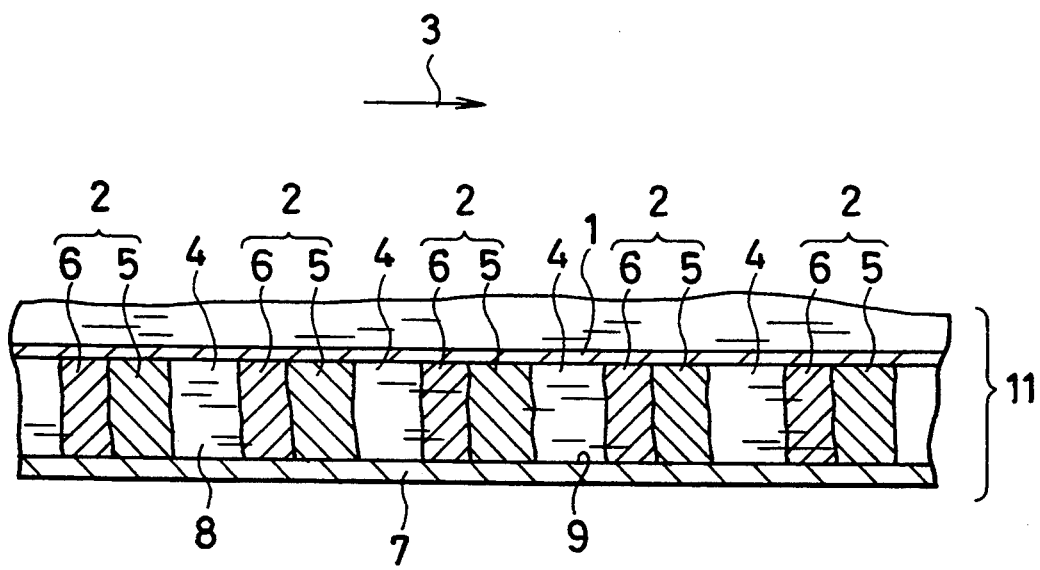
FIG. 1 is a longitudinal cross-sectional view of an embodiment of the microbody drive apparatus of the invention.

FIG. 1 illustrates a system using the microbody drive method according to this invention. A plurality of microscopic driven bodies 2 are affixed to the surface of a support 1 so that each of the driven bodies 2 faces toward the driving direction indicated by an arrow 3, and each of the driven bodies 2 is separated from the next by a prescribed space 4. The support 1 is for restricting the mutual positional relationship and orientation of the driven bodies 2, and as such it is preferable that the support 1 be formed of a material that is lyophilic, has a certain flexibility and strength and a very small volume and weight, such as a very fine fibroid or very thin sheet, for example, but which is shown thickened in the cross-section of the drawing. It goes without saying that, depending on the case, the support 1 may be omitted. With respect to the driving direction 3, each of the driven bodies 2 consists of an attachable portion 5 that is located at the front and adjoins a detachable portion 6 located at the rear. The attachable portion 5 and detachable portion 6 are both constituted of a flexible material that readily deforms to allow the body to be drawn into a close fit with the substrate 7 and is also hydrophobic, or the portions 5 and 6 may both be constituted of a hydrophilic material.

An explanation will first be made with reference to the case in which the attachable flexible portion 5 and detachable flexible portion 6 are both hydrophobic. The substrate 7 is disposed in a prescribed spaced relationship opposite the surface of the support 1 to which the driven bodies 2 are affixed. An aqueous liquid layer 8 is provided between the substrate 7 and support 1, and the driven bodies 2 are provided in the liquid layer 8 so that their upper surface is in contact with the support 1 and their lower surface is in contact with the substrate 7. To allow the driven bodies 2 connected by the support 1 to move along the substrate 7, the substrate 7 is provided with a surface 9 that extends in the driving direction 3, and is preferably in the form of a fixed surface such as a strip member or the like. The substrate 7 is formed of a material that can become hydrophobic at or below a certain low temperature region and shift back to being hydrophilic at or above a certain high temperature region. The detachable portion 6 of the driven bodies 2 is formed of a material that is hydrophobic at either the low temperature region or the high temperature region. In addition, each detachable portion 6 is formed so that it can be heated to a temperature that is in or above the high temperature region while the surrounding liquid layer 8 is maintained at the low temperature region. Concerning the method of heating a plurality of detachable portions at the same time and how to constitute the detachable portion 6, detachable portions 6 may be formed in a blackish color by adding carbon or the like, for example, and heated by being subjected to external infrared irradiation or the like. On the other hand, the attachable portions 5 are formed so that they stay at a temperature within the low temperature region even when said heating raises the temperature of the detachable portions 6 to or above the high temperature region. Therefore, the portion of the substrate 7 in contact with the detachable portions 6 is heated to the high temperature region and becomes hydrophilic.

The system is the same when the attachable portion 5 and detachable portion 6 are both formed of a hydrophilic material, except that instead of an aqueous liquid layer, an oily liquid layer 8 is provided between the substrate 7 and the support 1, and the detachable portion 6 is selectively heated to or above a certain temperature region to thereby cause only the portion of the substrate 7 in contact with the detachable portion 6 to reach a high temperature and become hydrophobic.

In a system 11 thus constituted, the detachable portions 6 of a plurality of driven bodies 2 are heated, whereby the mutual hydrophobic action of the driven bodies 2 causes the bodies to be driven intermittently along the surface 9 of the substrate 7 in the direction 3. Continuing the heating causes this driving to continue. Although heat from each detachable portion 6 is also transmitted to the adjoining attachable portion 5, because of the much higher heat conductivity of the substrate 7 the temperature of the attachable portion 5 does not reach the high temperature portion.

An arrangement may be used in which the plurality of detachable portions 6 are instead collectively heated by electromagnetic radiation. This could be done by forming the detachable portions 6 so that they resonate and are heated only at a certain electromagnetic frequency, and then subjecting the detachable portions 6 to electromagnetic radiation of the said frequency.

Alternatively, a chemical reaction could be utilized for the collective heating of multiple detachable portions 6. For example, this could be accomplished by using a system 11 in which the liquid layer 8 includes an endothermic reactive substance and having the detachable portions 6 contain a catalyst that promotes the endothermic reaction.

The operation when the driven bodies 2 shown in FIG. 1 are heated will now be explained, with reference to FIGS. 2 to 4. The explanation will first be made with reference to when the attachable portion 5 and detachable portion 6 are both hydrophobic. When the system 11 is heated, initially the substrate 7 is in a low temperature region and is therefore hydrophobic. As the attachable portions 5 and detachable portions 6 are also hydrophobic, as shown in FIG. 2, the attachable portion 5 and detachable portion 6 behave like a single hydrophobic body, and the force of the surface tension acting between the attachable portion 5 and the substrate 7, and between the detachable portion 6 and the substrate 7, gives rise to forces 16 and 17 that draw the attachable portion 5 and detachable portion 6 onto the adsorbing Surface portions 7a and 7b, respectively, where they are thereby held immobile.

Figure 2:
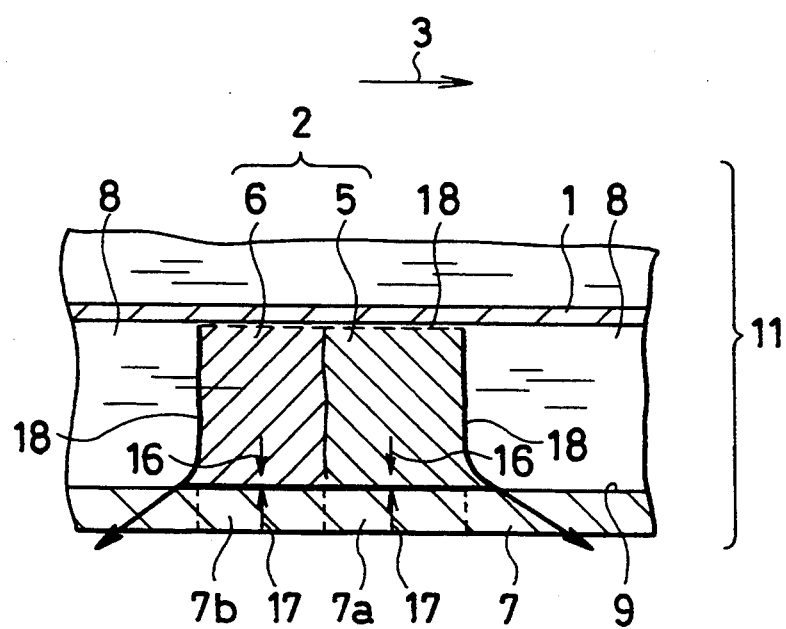
FIG. 2 shows a driven body adsorbed on the substrate.

When in the state shown in FIG. 2 the detachable portion 6 is heated to above a certain temperature, the heat thereof is transmitted to the surface portion 7b of the substrate 7 onto which the detachable portion 6 is drawn, whereby said surface portion is heated to a high temperature region. At that point, the surface portion 7b becomes hydrophilic, forming the transition portion 7t shown in FIG. 3, the water of the liquid layer 8 enters the interface between the transition portion 7t and the detachable portion 6, whereby the force drawing the transition portion 7t and the detachable portion 6 together ceases to act, causing the detachable portion 6 to detach from the substrate 7. However, even when it is subjected to heating the attachable portion 5 remains in the low temperature region, so that as the surface portion 7a on which the attachable portion 5 is drawn onto the substrate 7 remains in the low temperature region, the attachable portion 5 continues to be urged against the substrate 7. As described above, the attachable portion 5 and detachable portion 6 form a single driven body 2, and as the shape of the interface 18 (indicated by the thick line) between the liquid layer 8 and the driven body 2 is therefore extended more to the rear than in the case of FIG. 2, the force 14 exerted by the surface tension of the interface 18 ceases to act perpendicular to the substrate 7 and instead acts in a direction that compresses the interface 18, that is, diagonally down to the front. That is, the component of the surface tension force 14 that acts perpendicular to the substrate 7 and the force of the reaction thereto form the forces 16 and 17 that press the driven body 2 and substrate 7 together, but the component of the surface tension force 14 that acts in a direction parallel to the substrate 7 forms a sliding force 21 that pushes the body 2 forward in the direction 3. Multiple driven bodies 2 are affixed to the support 1 with each separated from the next by a space 4, and as the portion 7c of the substrate 7 immediately ahead of each attachable portion 5 is at a low temperature region and is therefore hydrophobic, the attachable portion 5 slides forward as it is drawn to the portion 7c ahead, while the trailing integral detachable portion 6 also slides forward as it is drawn to the hydrophobic surface portion 7a that the attachable portion 5 has left (FIG. 4). Following the detachment of the detachable portion 6, the transition portion 7t is cooled by the liquid layer 8 until it falls to within the low temperature region and becomes hydrophobic, thereby reverting to the state shown by FIG. 2. The distance between adjacent driven bodies 2 provided by the space 4 is such that it allows enough time for the hydrophobic transition to take place when the next attachment portion has reached the transition portion 7t.

Figure 3:
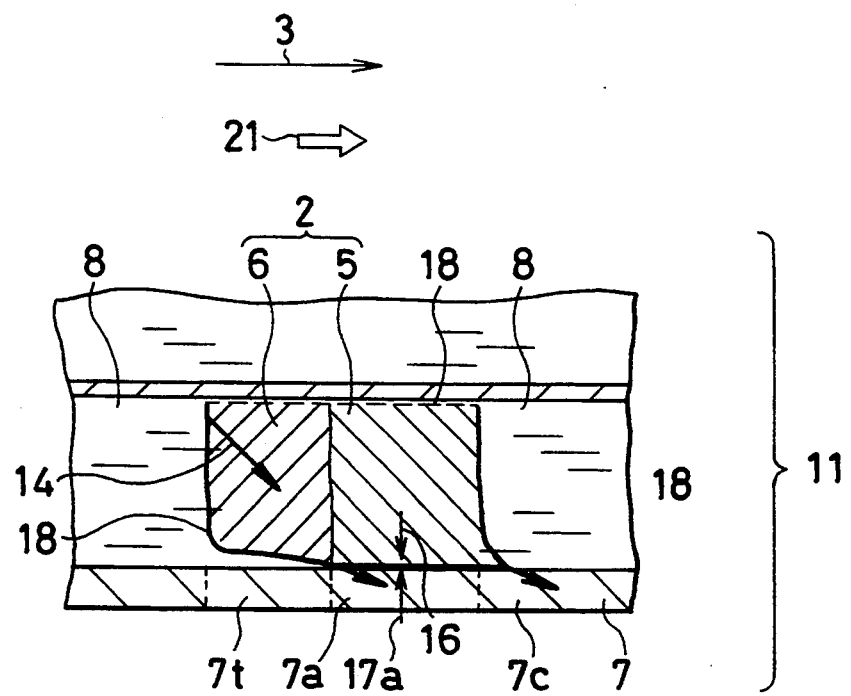
FIG. 3 shows when the detachable portion has detached from the substrate and the body is being urged forward.
Figure 4:
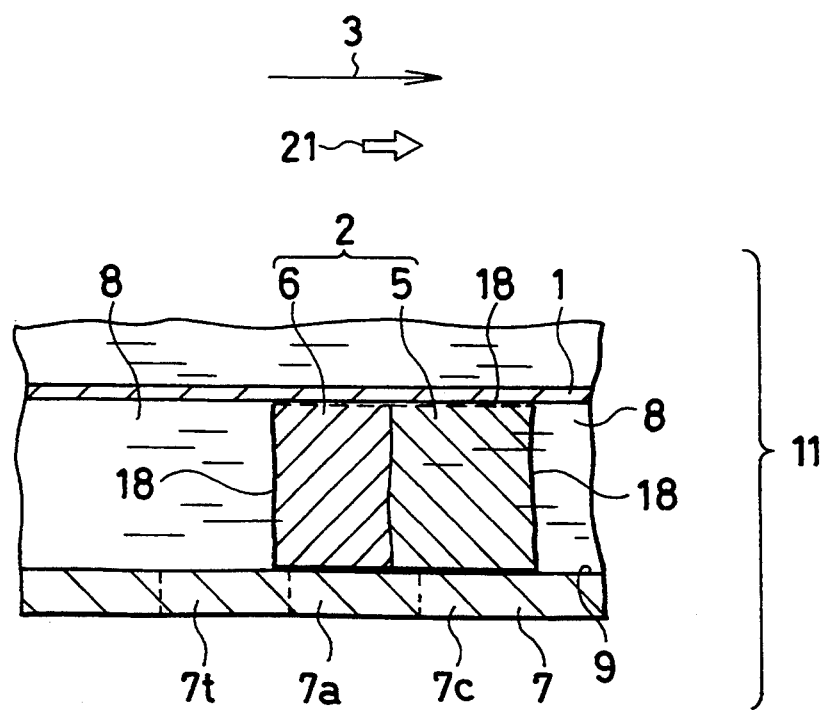
FIG. 4 illustrates the movement of a body.

Continuing the heating causes the system 11 to repeat the cycle of FIGS. 2 to 4, and this repetition causes the plurality of driven bodies 2, together with the support 1, to be moved along the substrate 7 in the direction 3.

Also in the case in which the attachable portion 5 and detachable portion 6 are both hydrophilic, the forces arising from the mutual lyophobic action of the attachable portion 5 and detachable portion 6 in the oily liquid layer 8, when overall heating is applied, result in the same operation with respect to the substrate 7, causing the driven bodies 2, with the support 1, to be moved along the substrate 7.

Concerning specific materials for forming the system 11 when the attachable portion 5 and detachable portion 6 are both hydrophobic, the substrate 7 can be formed of a polymer that is not water-soluble at low temperatures but dissolves at high temperatures, such as a copolymer of butyl methacrylate and acryl, or a polyamino acid that in a weakly acidic solution of poly-L-glutamic acid or the like assumes a helical structure at low temperatures and a coil structure at high temperatures. A hydrophobic gel such as poly-L-leucine or the like that has a helical structure at all the temperature regions concerned can be used to form the attachable portion 5 and detachable portion 6.

Concerning specific materials for forming the system 11 when the attachable portion 5 and detachable portion 6 are both hydrophilic, materials can be used such as the acrylamide based thermodielectric phase change polymers listed on page 92 of "The production and application of functional polymer gels," shown in Table 1, which exhibit hydrophilic properties at low temperatures and hydrophobic properties at high temperatures.

TABLE 1

| Polymer | Transition temp. (°C.) | Transition heat (cal/g) |
|---|---|---|
| poly-N-ethylacrylamide | 72 | — |
| poly-N-n-propylacrylamide | 21.0 | 11.6 |
| poly-N-n-propylmethacrylamide | 27.0 | 12.9 |
| poly-N-isopropylacrylamide | 30.0 | 11.1 |
| poly-N-isopropylmethacrylamide | 43.2 | 12.0 |
| poly-N-cyclopropylacrylamide | 45.2 | 3.5 |
| poly-N-cyclopropylmethacrylamide | 60.0 | 4.2 |
| poly-N-ethylmethylacrylamide | 56.0 | 5.0 |
| poly-N,N-diethylacrylamide | 32.0 | 6.3 |
| poly-N-acrylpyrrolidine | 56.0 | 1.9 |
| poly-N-acrylpiperidine | 5.5 | 10.0 |

Of these materials, selecting ones such as polyvinyl methyl ethyl and poly-N-isopropylacrylamide in which the transition between the hydrophilic and hydrophobic phases takes place at a temperature of about 30° C. to 40° C. facilitates controlling the drive speed. This is because while such materials are hydrophobic at a temperature well above the phase transition temperature, such as 50° C., for example, and hydrophilic at a temperature well below 30° C., for example 5° C., at a temperature region slightly higher than the phase transition temperature, such as 30° C. to 40° C., for example, changes in temperature produce a sharp increase in the degree of the hydrophobia. This is because a slight change in temperature from the collective heating can cause a major change in the ease of attachment of the detachable portion 6, so that by locating the system in a situation in which there is a slight fluctuation in the surrounding temperature the duration of the detachment of the detachable portion 6 can be increased, alleviating the usual tendency for the duration of the attachment period to be much shorter than the duration of the movement period.

As the hydrophilic material from which to form the attachable portion 5 and detachable portion 6, a flexible gel such as a polyacrylic gel may be used that has been swelled in water and exhibits hydrophilic properties over the full range of service temperatures.

That a body is drawn along a substrate by a mutually hydrophobic interaction can also be shown by the following simple experiment. Hydrophilic cellophane tape is adhered to one part of a strip made of a plastic such as Teflon or polyethylene which, with respect to hydrophobic properties, does not undergo a thermodielectrically induced phase change, the strip thus prepared is immersed in oil, and a drop of water is placed in the oil at the edge of the interface where the cellophane tape adheres to the strip. The drop of water will promptly move into the cellophane tape adhesion portion and spread out.

With the arrangement of this invention in which adjoining hydrophobic and hydrophilic portions are formed on a substrate and the hydrophobic interaction is used to move a body, the operation shown by the above experiment is continuously repeated on an autonomous basis.

In the method of driving microbodies according to this invention, the bodies are driven by the adsorbing force arising from the hydrophobic interaction, and the driving energy is obtained from light or electromagnetic radiation. With this invention, as there is no need to handle the driven bodies individually, multiple bodies ranging in size down to the nanometric can be collectively irradiated and driven by a very simple method without any need for bulky peripheral equipment for collimating light to a fine beam, and without having to undertake the difficult fabrication of fine electrodes or to use complex wiring arrangements.

What is claimed is:

1. A microscopic body driving method for driving a microscopic body formed of a solvent mixed gelled substance for relative displacement of said microscopic body with respect to another body, comprising intermittently generating in the microscopic body hydrophobic adsorption relative to the other body and generating a gradient by hydrophobic adsorption between front and rear portions of the microscopic body.

2. A microscopic body driving method for driving a microscopic body comprising:
providing a substrate of a material that is hydrophobic at a low temperature region and hydrophilic at a high temperature region and on which at least one body to be driven is arranged facing a prescribed direction, and providing as said body to be driven an attachable flexible portion disposed in a direction of forward movement and a detachable flexible portion adjoining a rear of the attachable flexible portion, wherein the attachable flexible portion and detachable flexible portion are both formed of a material that is hydrophobic at the low temperature region and at the high temperature region, the method further including immersing the substrate and body to be driven in an aqueous liquid; and
selectively heating the detachable flexible portion while the substrate and body to be driven are maintained in the low temperature region except for a portion of the substrate which is locally heated by the detachable flexible portion, such that said portion of said substrate becomes hydrophilic.

3. A microscopic body driving method for driving a microscopic body comprising:
providing a substrate of a material that is hydrophobic at a low temperature region and hydrophilic at a high temperature region and on which at least one body to be driven is arranged facing a prescribed direction, and providing as said body to be driven an attachable flexible portion disposed in a direction of forward movement and a detachable flexible portion adjoining a rear of the attachable flexible portion, wherein the attachable flexible portion and detachable flexible portion are both formed of a material that is hydrophilic at the low temperature region and at the high temperature region, and immersing the substrate and body to be driven in an oily liquid; and
selectively heating the detachable flexible portion while the substrate and body to be driven are maintained in the low temperature region except for a portion of said substrate which is locally heated by the detachable flexible portion such that said portion of said substrate becomes hydrophilic.

4. A microscopic body driving method according to claim 2 or 3, further including providing multiple bodies to be driven which are supported by a support member facing in a prescribed direction.

5. A microscopic body driving method according to claim 2 or 3, wherein the step of heating of the detachable flexible portion is effected by subjecting the detachable flexible portion to light or electromagnetic radiation.

6. A microscopic body driving method according to claim 2 or 3, wherein the step of heating of the detachable flexible portion is effected by means of a chemical reaction with the liquid layer.

7. A microscopic body drive apparatus, comprising:
a substrate formed of a material that is hydrophilic at a low temperature region and hydrophobic at a high temperature region;
at least one body to be driven arranged on the substrate facing a prescribed direction;
said body to be driven comprising an attachable flexible portion disposed in a direction of forward movement and a detachable flexible portion adjoining a rear of the attachable flexible portion, said attachable flexible portion and detachable flexible portion both being formed of a hydrophobic material;
an aqueous liquid into which the substrate and the body to be driven are both immersed which maintains at least part of the substrate at a low temperature region; and
means for selectively heating the detachable flexible portion whereby the portion of the substrate in contact with the detachable flexible portion is heated to cause it to become hydrophilic.

8. A microscopic body drive apparatus, comprising a substrate formed of a material that is hydrophilic at a low temperature region and hydrophobic at a high temperature region, at least one body to be driven arranged on the substrate facing a prescribed direction, said body to be driven being comprised of an attachable flexible portion disposed in a direction of forward movement and a detachable flexible portion adjoining the rear of the attachable portion, said attachable flexible portion and detachable flexible portion both being formed of a hydrophilic material, an oily liquid into which the substrate and the body to be driven are both immersed which maintains at least part of the substrate at a low temperature region, and means for selectively heating the detachable flexible portion whereby the portion of the substrate in contact with the detachable flexible portion is heated to cause it to become hydrophilic.

9. The drive apparatus according to claim 7 or 8, wherein the substrate is formed of a fixed polyamino acid.

10. The drive apparatus according to claim 7 or 8, wherein the attachable flexible portion and detachable flexible portion are formed of a poly-L-leucine gel.

11. The drive apparatus according to claim 7 or 8, wherein the substrate is formed of polyvinyl methyl ethyl or poly-N-isopropylacrylamide.

12. The drive apparatus according to claim 7 or 8, wherein the attachable flexible portion and detachable flexible portion are formed of a polyacrylic gel compound.

13. The drive apparatus according to claim 7 or 8, wherein the heating means includes light irradiation means.

14. The drive apparatus according to claim 7 or 8, wherein the heating means includes electromagnetic irradiation means.

15. The drive apparatus according to claim 7 or 8, wherein there are multiple bodies to be driven which are supported by a support member facing in a prescribed direction.

* * * * *